(12) United States Patent
Li

(10) Patent No.: US 10,182,948 B2
(45) Date of Patent: Jan. 22, 2019

(54) METHOD AND DEVICE FOR MAKING ABSORBENT CORES USED IN DISPOSABLE HYGIENE PAD

(75) Inventor: Qiuhong Li, Beijing (CN)

(73) Assignee: Beijing Beishute Maternity & Child Articles Co., Ltd. (CN)

(*) Notice: Subject to any disclaimer, the term of this patent is extended or adjusted under 35 U.S.C. 154(b) by 724 days.

(21) Appl. No.: 14/357,156

(22) PCT Filed: Aug. 16, 2012

(86) PCT No.: PCT/CN2012/080205
§ 371 (c)(1),
(2), (4) Date: May 8, 2014

(87) PCT Pub. No.: WO2014/026346
PCT Pub. Date: Feb. 20, 2014

(65) Prior Publication Data
US 2014/0308483 A1 Oct. 16, 2014

(51) Int. Cl.
*A61F 13/15* (2006.01)
*A61F 13/535* (2006.01)
(Continued)

(52) U.S. Cl.
CPC .... *A61F 13/15658* (2013.01); *A61F 13/1565* (2013.01); *A61F 13/15626* (2013.01);
(Continued)

(58) Field of Classification Search
CPC .......... A61F 13/15634; A61F 13/15674; A61F 13/15658; A61F 13/15699;
(Continued)

(56) References Cited

U.S. PATENT DOCUMENTS 4,715,918 A    12/1987   Lang
5,458,592 A *  10/1995   Abuto .................. A61F 13/531
                                                          156/167
(Continued)

FOREIGN PATENT DOCUMENTS

CN          1976663      6/2007
CN        101404970      4/2009
(Continued)

OTHER PUBLICATIONS

Search Report issued in Int'l App. No. PCT/CN2012/080205 (dated 2013).

*Primary Examiner* — Michael N Orlando
*Assistant Examiner* — Marta S Dulko
(74) *Attorney, Agent, or Firm* — Barnes & Thornburg LLP

(57) ABSTRACT

The invention relates to a method and a device for making absorbent cores used in disposable hygiene pads, the method or device comprising three steps: (A) suctioning of wood pulp fibers mixed with super absorbent polymers into a net structure on a base tissue to form an absorbent core; (B) compressing and embossing absorbent material; and (C) shaping of the absorbent core. The method of the current invention can be used for making different kinds of absorbent pad products. While increasing the tear strength of the product, the method realizes and simplifies the process of making both the absorbent material and the hygiene pad utilizing the absorbent material on the same manufacturing line, and reduces the cost of making the absorbent pads. The absorbent core made by applying the method of the current invention has a new structure formed by super absorbent polymers and wood pulp fibers, wherein the structure enables the super absorbent polymers to be evenly distributed in between the wood pulp fibers. Through the compressing and embossing process, the super absorbent poly- (Continued)

mers are prevented from sliding or piling together in the absorbent core, which increases the liquid-absorbing capacity of the hygiene pad products.

1 Claim, 3 Drawing Sheets

(51) Int. Cl.
 A61F 13/536 (2006.01)
 A61F 13/53 (2006.01)
(52) U.S. Cl.
 CPC .......... *A61F 13/535* (2013.01); *A61F 13/536* (2013.01); *A61F 2013/530124* (2013.01); *Y10T 156/1051* (2015.01); *Y10T 428/2457* (2015.01)
(58) Field of Classification Search
 CPC .............. A61F 13/15617; A61F 13/535; A61F 13/15682; A61F 13/1565; A61F 2013/530562
 See application file for complete search history.

(56) References Cited

U.S. PATENT DOCUMENTS

| | | | |
|---|---|---|---|
| 5,494,622 A | 2/1996 | Heath et al. | |
| D408,541 S | 4/1999 | Dunshee | |
| D409,754 S | 5/1999 | Dunshee | |
| 6,048,489 A * | 4/2000 | Reiter | A61F 13/532 264/113 |
| D430,674 S | 9/2000 | Dunshee | |
| D454,955 S | 3/2002 | Dunshee | |
| D458,687 S | 6/2002 | Dale | |
| 6,410,820 B1 * | 6/2002 | McFall | A61F 13/15203 604/369 |
| 6,675,702 B1 | 1/2004 | Maksimow | |
| D493,230 S | 7/2004 | Liedtke | |
| D572,824 S | 7/2008 | Propp | |
| D576,282 S | 9/2008 | Yanaki | |
| 7,619,130 B2 | 11/2009 | Nielsen | |
| 7,717,150 B2 | 5/2010 | Manabe et al. | |
| D620,123 S | 7/2010 | Igwebuike | |
| D679,402 S | 4/2013 | Conrad-Vlasak | |
| D679,403 S | 4/2013 | Heinecke | |
| D683,858 S | 6/2013 | Smith | |
| D687,555 S | 8/2013 | Peterson | |
| D688,377 S | 8/2013 | Heinecke | |
| D690,425 S | 9/2013 | Heinecke | |
| D693,010 S | 11/2013 | Mosa | |
| D695,901 S | 12/2013 | Heinecke | |
| D723,176 S | 2/2015 | Igwebuike | |
| D723,177 S | 2/2015 | Igwebuike | |
| D729,391 S | 5/2015 | Igwebuike | |
| 2002/0087106 A1 | 7/2002 | Unger | |
| 2004/0138601 A1 | 7/2004 | Chalmers | |
| 2004/0241214 A1 | 12/2004 | Kirkwood | |
| 2005/0159694 A1 | 7/2005 | Berndt | |
| 2005/0159695 A1 | 7/2005 | Cullen | |
| 2006/0003133 A1 | 1/2006 | Johnson | |
| 2006/0011030 A1 * | 1/2006 | Wagner | B26D 7/20 83/343 |
| 2007/0003606 A1 | 1/2007 | Booher | |
| 2007/0044903 A1 * | 3/2007 | Wisneski | A61F 13/1565 156/204 |
| 2007/0077841 A1 * | 4/2007 | Zoch | A61F 13/531 442/340 |
| 2008/0038504 A1 | 2/2008 | Manabe et al. | |
| 2009/0082710 A1 | 3/2009 | Vitaris | |
| 2009/0227968 A1 | 9/2009 | Vess | |
| 2009/0234306 A1 | 9/2009 | Vitaris | |
| 2009/0234309 A1 | 9/2009 | Vitaris | |
| 2009/0270823 A1 | 10/2009 | Meizelman | |
| 2010/0022978 A1 | 1/2010 | Kasai et al. | |
| 2011/0046587 A1 | 2/2011 | Meizelman | |
| 2012/0165715 A1 | 6/2012 | Murphy | |
| 2012/0197173 A1 | 8/2012 | Babitz | |
| 2012/0238932 A1 | 9/2012 | Atteia | |
| 2013/0014899 A1 | 1/2013 | Nakano | |
| 2014/0058309 A1 | 2/2014 | Addison | |
| 2014/0107561 A1 | 4/2014 | Dorian | |
| 2014/0358058 A1 | 12/2014 | Nelson | |

FOREIGN PATENT DOCUMENTS

| | | |
|---|---|---|
| CN | 101797201 | 8/2010 |
| CN | 102098994 | 6/2011 |
| EP | 2308432 | 4/2011 |
| WO | WO 1999/025281 | 5/1999 |
| WO | WO 2011/092935 | 8/2011 |

* cited by examiner

METHOD AND DEVICE FOR MAKING ABSORBENT CORES USED IN DISPOSABLE HYGIENE PAD

CROSS REFERENCE TO RELATED APPLICATIONS

This application is a U.S. nationalization under 35 U.S.C. § 371 of International Application No. PCT/CN2012/080205, filed Aug. 16, 2012. The disclosure set forth in the referenced application is incorporated herein by reference in its entirety.

FIELD OF THE INVENTION

The invention relates to the field of health care products having an absorbent nature. Specifically, the invention introduces a method and device for making absorbent cores used in disposable hygiene pads.

BACKGROUND OF THE INVENTION

As is commonly known in the field, wood pulp fibers and super absorbent polymers can be made into absorbent paper through a binding process by heat or glue to be used as the absorbent material in hygiene pads, wherein the absorbent paper can satisfy the liquid-absorbing goal of the hygiene pads. Several advantages exist in using absorbent paper as the absorbent material in hygiene pads: the super absorbent polymers are placed evenly in the absorbent material used in hygiene pad products; the super absorbent polymers are fixed tightly inside the absorbent material; and the absorbent capacity of the hygiene pads using the absorbent material is high.

Drawbacks also exist in using absorbent paper as the absorbent material in hygiene pads, such as the speed of making absorbent paper is low. For instance, the speed of making absorbent paper is 50-70 meters/min using current technology and the speed of making hygiene pads is 120-180 meters/min and therefore, it is impossible to make absorbent paper while simultaneously make hygiene pads on one manufacturing line. Therefore, it is required to produce the absorbent paper in advance using one device and then put the absorbent paper into another device to make hygiene pad products; thus the cost of using this method is very high. Moreover, the length of each roll of the pre-made absorbent paper may be limited and, therefore, a manufacturer has to constantly change the rolls of the absorbent paper. Furthermore, this causes more waste and lowers the quality of the final products. Additionally, using pre-made absorbent paper requires additional packaging, storage and transportation before it can be put into the device used to manufacture hygiene pads and therefore, it causes negative consequences such as an increased cost to make hygiene pads, greater risks in affecting the quality of the hygiene pads, and more potential safety hazards.

A method and technology of making absorbent paper is disclosed in the international patent application WO1999/025281, wherein "the fabric material" stated in the application is a type of the absorbent paper referred in our field of industry.

Another method that the industry currently uses for manufacturing absorbent material is to make the absorbent material on the same manufacturing line that is manufacturing the hygiene pads. One advantage of this method is that the production speed is high, wherein the speed in making absorbent material can reach 120-180 meters/min. The cost is also low and the superior product rate is high because the manufacturing of the absorbent material and the final hygiene pads can be made continuously on the same manufacturing line.

However, unlike the absorbent material using absorbent paper, the wood pulp fibers and the super absorbent polymers in the absorbent material produced by this method may not be evenly distributed. Moreover, less super absorbent polymers can be put into the absorbent material made by this method, and the super absorbent polymers may not be tightly fixed inside the absorbent material such that the super absorbent polymers could move around and pile together inside the pad. Consequently, the absorbent material's capability to absorb liquid may be greatly decreased by this method. Additionally, the hygiene pad using the absorbent material may not consistently absorb liquid and therefore, the comfort level provided to the user by the hygiene pad made with such absorbent material is relatively low.

As the supply of natural resources becomes more and more limited, hygiene pads are developed to be manufactured with a lighter and thinner design. To make lighter and thinner hygiene pads, it is desired to have a smaller amount of wood pulp fibers and a much larger amount of super absorbent polymers in the absorbent material. Moreover, when making absorbent materials and hygiene pads on the same manufacturing line, the process of simply increasing the amount of super absorbent polymers used by the traditional method does not achieve the same liquid-absorbing function provided by the hygiene pads using absorbent paper as the absorbent material.

The current invention has found a way to develop a new method that successfully incorporates the manufacturing of absorbent paper into one manufacturing line that is also used to manufacture hygiene pads, achieving the result of a more consistent liquid-absorbing function while largely reducing the cost of production.

DISCLOSURE OF THE INVENTION

The technical issue that the current invention has resolved is to provide a developed method to make absorbent cores used in hygiene pads. Applying this method, one can make absorbent cores on the same manufacturing line that makes hygiene pads and use the absorbent cores instead of commonly used absorbent paper. In the process of making the absorbent core, wood pulp fibers are able to be placed evenly inside the absorbent core by improving the device to introduce wood pulp fibers. The super absorbent polymers are able to be placed evenly inside the absorbent core by improving the device to introduce super absorbent polymers. The wood pulp fibers and the super absorbent polymers are mixed evenly by adopting a developed method. The absorbent core is compressed and embossed by a special embossing device to create a desired embossed pattern on the absorbent core, wherein the embossed pattern creates a three dimensional net-structured space to prevent the super absorbent polymers from moving or piling up at a certain location inside the absorbent core. This permits the absorbent core to maintain a normal liquid-absorbing condition and realize the maximum liquid-absorbing capability of the super absorbent polymers. The issue that hygiene pads are unable to consistently absorb liquid has been improved by the method and the device of the current invention.

To resolve the issue described above, a detailed description of the current invention is as follows:

A method for making absorbent cores to be used in hygiene pads comprising the following steps:

(a) the suction of wood pulp fibers which are mixed with super absorbent polymers: a base tissue 2 moves along with a transmitting belt on a suction bed 1 which has negative pressure on its surface; rolls of wood pulp 3 are shredded into wood pulp fibers by a wood pulp shredder 5, and the wood pulp fibers fall with the airflow in the wood pulp fiber container 4 and are sucked tightly on top of the base tissue 2 by the negative pressure on the surface of the suction bed 1, wherein the wood pulp fibers form a net structure on top of the base tissue 2. Super absorbent polymers in a super absorbent polymer container 6 fall evenly as a distributing roll 7 rotates. As the base tissue 2 moves, the falling super absorbent polymers are sucked into the space in the net structure formed by the wood pulp fibers on top of the base tissue 2 by the negative pressure from the surface of the suction bed 1. The super absorbent polymers are mixed thoroughly with the wood pulp fibers and a top tissue 8 is placed to cover the wood pulp fibers and the super absorbent polymers. To resolve the issue that wood pulp fibers cannot be placed evenly by applying traditional methods, the current invention increases the size of a bottom hole of the wood pulp fiber container 4 and added an airflow control plate to adjust the volume of the airflow, so that the airflow inside the wood pulp fiber container 4 can be adjusted when necessary to ensure that the airflow generated from the wood pulp fiber shredder is coordinated with the airflow generated from the negative pressure on top of the suction bed 1. This ensures that the wood pulp fibers are placed evenly on top of the base tissue 2. To resolve the issue that the super absorbent polymers cannot be distributed evenly by applying traditional methods making absorbent materials, the current invention improves the design of the distributing roll 7, wherein the surface of the distributing roll 7 has evenly distributed semi-circular dents for holding super absorbent polymers. The super absorbent polymers fall into the dents and then fall away as the distributing roll 7 rotates under the super absorbent polymer container 6. The super absorbent polymers are introduced into the net structure formed by the wood pulp fibers as the base tissue 2 moves. Therefore, the issue that super absorbent polymers cannot be thoroughly mixed with the wood pulp fibers is successfully addressed. To address the issue that the quantity of super absorbent polymers added by using traditional methods is relatively low, the current invention improves the design of the distributing roll 7, wherein the distributing roll 7 is controlled by an independent rotating electronic motor and the rotating speed is controlled by an adjustable speed-frequency device. Therefore, the quantity of the super absorbent polymers introduced into the absorbent core can be adjusted to meet the needs of different products for increasing the content of super absorbent polymers. Therefore, the issue that only low quantity of super absorbent polymers can be placed into the absorbent cores is addressed.

(b) the absorbent core is compressed and embossed: the top tissue 8 and the base tissue 2 cover the mixture of the super absorbent polymers and the wood pulp fibers to form a pre-compressed absorbent core, and a transitional roll directs the top tissue 8 and provides a preliminary compression on the pre-compressed absorbent core to form a first compressed absorbent core. A folding sector 10 folds the edges of the first compressed absorbent core to completely wrap the mixture of the super absorbent polymers and the wood pulp fibers to prevent the hygiene pads from leaking when being used. A bottom compressing roll 11.2 and a top compressing roll 11.1 compress on the edge-folded first compressed absorbent core for another time. Both the top compressing roll 11.1 and the bottom compressing roll 11.2 may have a smooth surface, and both may be used to reduce the required pressure from a top embossing roll 12.1 and a bottom embossing roll 12.2 and to preliminarily prevent the super absorbent polymers from moving inside the absorbent core. The surface of the bottom embossing roll 12.2 may be smooth and the surface of the top embossing roll 12.1 may have evenly distributed studs. The coordination of the embossing rolls 12.1 and 12.2 completes embossing on the absorbent core. The top of the absorbent core may be embossed with a pattern wherein every square centimeter has 1-2 grids of the pattern such that the wood pulp fibers form a three dimensional net-structured space in which super absorbent polymers are completely locked inside the space. To enable the three dimensional net structured space formed by the wood pulp fibers to have a relatively high tear strength, the current invention utilizes the compressing and embossing rolls to subject the absorbent core to pressure and heat.

(c) The shaping of the absorbent core: the absorbent core is cut by a cutter into separate pieces, and the cut absorbent core is transported by a flat moving belt to the next step for complete making the hygiene pad. Under the current step, the bottom cutting roll 14.2 may be made of a material having a relatively high hardness. The surface of the bottom cutting roll 14.2 may be smooth and the surface of the top cutting roll 14.1 may have a cutter. The bottom cutting roll 14.2 and the cutter on the top cutting roll 14.2 work together to complete cutting of the absorbent core. To decrease the extent of abrasion of the cutter and to prevent the cutter from always cutting at the same location on the bottom cutting roll 14.2, the diameter of the top cutting roll 14.1 may be longer than the diameter of the bottom cutting roll 14.2. A first flat moving belt 13 is the platform for transmitting the absorbent core, wherein negative pressure is utilized on the surface of the flat moving belt 13. The cut absorbent core 100 may be transmitted to the next manufacturing step by a second flat moving belt 15 for completing the production of the hygiene pad.

The devices used to realize the method for making hygiene pads by the current invention comprises: a suction bed 1 having negative pressure on its surface; a transmitting belt for holding a base tissue 2 carrying wood pulp fibers is located on top of the suction bed 1 a wood pulp shredder 5 for shredding a roll of wood pulp into the wood pulp fibers; a wood pulp fiber container 4 are located above the suction bed 1, wherein wood pulp fibers fall with the airflow inside the wood pulp fiber container 4. The negative pressure from the surface of the suction bed 1 sucks the wood pulp fibers tightly on the base tissue 2 to form a net structure. A distributing roll 7 for evenly placing the super absorbent polymers is located above the suction bed 1, and a super absorbent polymer container 6 is placed above the distributing roll 7. The super absorbent polymers are distributed evenly as the distributing roll 7 rotates. The super absorbent polymers are sucked into the space of the net structure formed by wood pulp fibers by the negative pressure from the surface of the suction bed 1. Therefore, the super absorbent polymers are well mixed with the wood pulp fibers.

The current device further comprises a transitional roll for preliminary compressing the mixture of the wood pulp fibers and the super absorbent polymers, the mixture covered by the top tissue 8 and the base tissue 2, to form a first compressed absorbent core.

The current device further comprises a folding sector 10 for folding the edges of the first compressed absorbent core after the preliminary compression, wherein the absorbent core is completely wrapped by tissues so that the hygiene pad is prevented from leaking wood pulp fibers and super absorbent polymers when being used.

The current device further comprises a bottom compressing roll 11.2 and a top compressing roll 11.1 configured to compress the edge-folded first compressed absorbent core a second time, wherein the bottom compressing roll 11.2 and the top compressing roll 11.1 may be connected by a synchronous gear.

The current device further comprises a bottom embossing roll 12.2 and a top embossing roll 12.1 for embossing on the compressed absorbent core, wherein the surface of the bottom embossing roll 12.2 may be smooth and made of stainless steel. The bottom embossing role 12.2 works together with the top embossing roll 12.1 to complete embossing on the absorbent core, wherein the surface of the top embossing roll 12.1 may have evenly distributed studs.

The current device further comprises a cutting device for cutting the compressed and embossed absorbent core, wherein the cutting device comprises a bottom cutting roll 14.2 and a top cutting roll 14.1, The bottom cutting roll 14.2 may be made of a material of relatively high hardness, and the surface of the bottom cutting roll 14.2 may be smooth. The bottom cutting role 14.2 is configured to work together with the cutter on the surface of the top cutting roll 14.1 to cut the absorbent core into separate pieces. The diameter of the top cutting roll 14.1 may be greater than the diameter of the bottom cutting roll 14.2 to prevent the cutter from always cutting on the same place on the bottom cutting roll 14.2.

The current device further comprises a first flat moving belt 13 for moving the absorbent core 100. The current device may also comprise a second flat moving belt 15, and a device that generates negative pressure connected to the flat moving belts.

An absorbent core, made by the method and device mentioned above.

The positive results that may be achieved by the current invention are: the method described by the current invention is suitable for making various kinds of hygiene pads, wherein the current invention simplifies the line of production for making absorbent core and the hygiene pad on the same production line while maintaining the tear strength of the hygiene pad products. Due to the improvement achieved by the current invention for making absorbent core, super absorbent polymer materials are evenly mixed into the space between the wood pulp fibers while the wood pulp fibers are moving on the production line. The current method does not add heat melt glue into the production process, and the super absorbent polymers are distributed evenly in the wood pulp fibers. The new three dimensional net-structured space formed by wood pulp fibers prevented the super absorbent polymer materials from sliding and piling up inside the absorbent core, and additionally, the net-structured space is able to increase the content of the super absorbent polymers that can be mixed inside the wood pulp fibers. Applying the method described by the current invention, the biggest ratio of the content of the super absorbent polymers versus the content of the wood pulp fibers inside the absorbent core may be 1:2. Increasing the content of super absorbent polymers in the absorbent core may result in enhancing the liquid-absorbing capability of the absorbent core, which significantly increases the amount of liquid that can be absorbed by the hygiene pad. The hygiene pad made by the current invention can absorb liquid more consistently on the surface and has an extremely strong capability to absorb liquid with a strong tear strength while keeping the surface of the hygiene pad soft and comfortable. This is a feasible method and device of continuously making hygiene pads for the industry. The absorbent core made by the current invention may weigh 80-500 grams for every $m^2$ of the absorbent core, wherein the structure of the absorbent core becomes stronger because of the compression and embossing that increases the tear strength of the absorbent core. The tear strength of the machine direction of the absorbent core can normally reach 0.015 KN/m.

The current invention enhances the method for making products using absorbent paper and the traditional method for making hygiene pad products. The current invention provides a new method and device for making absorbent cores and the hygiene pad on the same production line, which significantly reduced the cost for making hygiene pads. Based on a real manufacturing statistics, compared to the method of using absorbent paper as the absorbent material, applying the current method for making absorbent core increases the rate of quality for making hygiene pads %-8%. The cost for raw materials for making the absorbent core may also be reduced 20%-25%. Thus, the overall reduced cost may be 12%-15%.

DESCRIPTION OF THE PREFERRED EMBODIMENTS

The preferred embodiments of the current invention will hereby be described according to the figures of the drawings.

Figure 1:
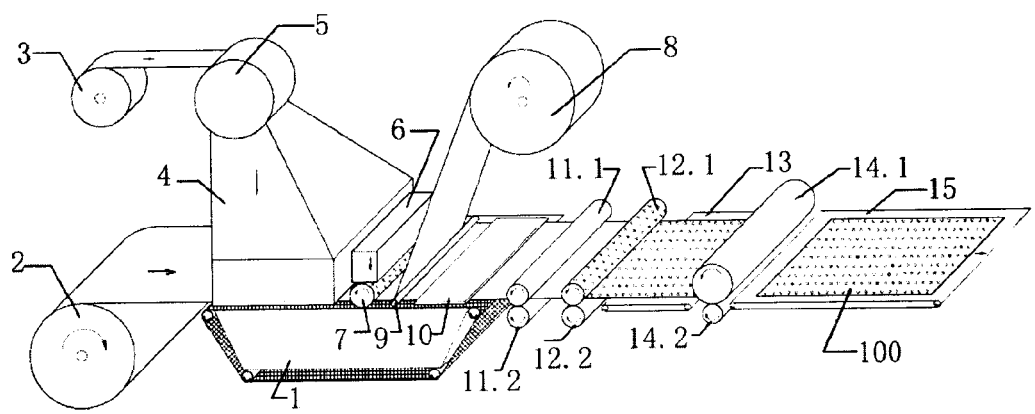
FIG. 1 is a schematic representation of a device for making absorbent cores of the present disclosure.

As shown in FIG. 1, the device for realizing the current method for making absorbent cores used in hygiene pads comprises a suction bed 1 with a surface that has negative pressure and a transmitting belt on the suction bed 1 for holding a base tissue 2 carrying wood pulp fibers. The device further comprises a wood pulp shredder 5 placed above the suction bed 1 for shredding rolls of wood pulp 3 into wood pulp fibers. The wood pulp shredder 5 is connected to a wood pulp fiber container 4, wherein the wood pulp fibers are carried by the airflow generated from the spinning motion of the wood pulp shredder and are also drawn by the suction airflow from the surface of the suction bed. Specifically, the wood pulp fibers fall down inside the wood pulp fiber container 4, and are sucked onto the base tissue 2 by the negative pressure on the surface of the suction bed 1, forming a net structure.

The device further comprises a distributing roll 7 for evenly placing super absorbent polymers. The distributing roll 7 is placed above the suction bed 1, and a super absorbent polymer container 6 is placed above the distributing roll 7. The super absorbent polymers fall down evenly as the distributing roll 7 rotates, and the super absorbent polymers are sucked into the space in the net structure formed between the wood pulp fibers by the negative pressure from the surface of the suction bed 1, thoroughly mixing the super absorbent polymers with the wood pulp fibers.

The current device further comprises a transitional roll 9 creates a preliminary compression on the mixture of the wood pulp fibers and the super absorbent polymers. The transition roll 9 also distributes a top tissue 8. The transition roll 9 creates preliminary compression on the top tissue 8 and the base tissue 2, forming a first compressed absorbent core.

The current device further comprises a folding sector 10 for folding the edges of the first compressed absorbent core. The folding sector 10 ensures the absorbent core is completely covered by tissues, preventing the wood pulp fibers or the super absorbent polymers from falling out when using the hygiene pads.

The current device further comprises a bottom compressing roll 11.2 and a top compressing roll 11.1 for compressing on the folded-edge absorbent core a second time. The second compression forms a second compressed absorbent core. The bottom compressing roll 11.2 and the top compressing roll 11.1 may be connected by a synchronous gear.

The current device further comprises a top embossing roll 12.1 and a bottom embossing roll 12.2 for compressing and embossing on the second compressed absorbent core. The surface of the bottom embossing roll 12.2 may be smooth and made of stainless steel. The bottom embossing roll 12.2 works in coordination with the top embossing roll 12.1 to complete the embossing process. The surface of the top embossing roll 12.1 may have evenly distributed studs.

The current device further comprises a cutter for cutting the compressed and embossed absorbent core into separate pieces, the cutter comprising a bottom cutting roll 14.2 and a top cutting roll 14.1. The bottom cutting roll 14.2 may be made of a material of relatively high hardness. The surface of the bottom cutting roll 14.2 may be smooth. The bottom cutting roll 14.2 and the top cutting roll 14.1 work in coordination for cutting the absorbent core into separate pieces. To prevent the cutting knife from always cutting on the same place on the bottom cutting roll 14.2, the diameter of the top cutting roll 14.1 may be bigger than the diameter of the bottom cutting roll 14.2.

The current device further comprises a first flat moving belt 13 and a second flat moving belt 15 for transporting the absorbent core 100 to the next production step. A device generating negative pressure may be connected to the flat moving belts.

The method for making absorbent cores used in hygiene pad products may comprise the following steps:

A. Suctioning of wood pulp fibers which are mixed with super absorbent polymers through the following steps:

a base tissue 2 moves along on a transmitting belt on a suction bed 1 that has negative pressure on its surface;

rolls of wood pulp 3 are shredded into wood pulp fibers by a wood pulp shredder 5, the wood pulp fibers falling with the airflow inside a wood pulp fiber container 4;

the wood pulp fibers are sucked tightly on top of the base tissue 2 by the negative pressure from the surface of the suction bed 1, wherein the wood pulp fibers form a net structure on top of the base tissue;

super absorbent polymers inside a super absorbent polymer container 6 are introduced onto the top of the moving base tissue by the rotation of a distributing roll 7, wherein the super absorbent polymers are evenly sucked and drawn into a space of the net structure formed by the wood pulp fibers, and are covered by a top tissue 8.

Figure 2:
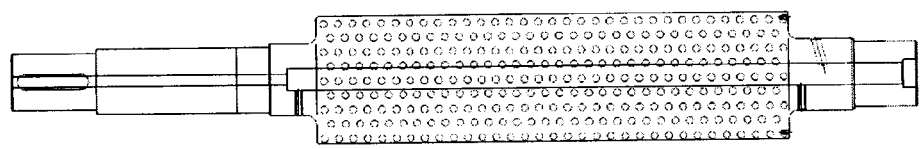
FIG. 2 is a representation of a distributing roll.
Figure 3:
FIG. 3 is an enlarged representation showing the cross section of the surface of the distributing roll.
Figure 4:
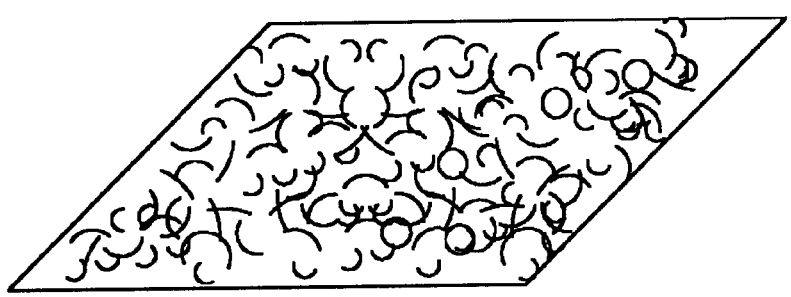
FIG. 4 is an enlarged representation showing the distribution of wood pulp fibers on a base tissue.

As shown in FIG. 2 and FIG. 3, the distributing roll has a smooth surface made of stainless steel, having a cylinder shape. When the humidity in the environment reaches 50% or higher, the volume of the super absorbent polymers will expand by absorbing moisture in the air due to its liquid-absorbing nature. Therefore, a heating device may be placed inside the distributing roll 7 to reduce the humidity in its surrounding environment such that the super absorbent polymers are kept dry. The surface of the distributing roll 7 has specially designed dents (as shown in FIG. 3) for continuously storing super absorbent polymers. The dents are for storing super absorbent polymers, wherein the super absorbent polymers fall into the dents and then fall away as the distributing roll 7 rotates under the super absorbent polymer container 6. The super absorbent polymers evenly fall into the space of the net structure formed by the wood pulp fibers being moved forward (as shown in FIG. 4). The wood pulp fibers are relatively loose and the super absorbent polymers have a slippery nature, therefore, the super absorbent polymers are easily slipped into the space in the net structure formed by the wood pulp fibers when sucked by the strong negative pressure from the surface of the suction bed 1. Therefore, the super absorbent polymers are mixed thoroughly with the wood pulp fibers. To control the amount of super absorbent polymers being introduced, the distributing roll may be controlled by an independent motor, wherein an adjustable-speed-frequency device may be connected to a PLC on the manufacturing line to ensure that the amount of super absorbent polymers introduced are kept consistent.

The current method enables the super absorbent polymers to be evenly mixed into the space of the wood pulp fibers as the wood pulp fibers are being transported forward, to realize a thorough mixture of the super absorbent polymers and the wood pulp fibers. Applying the current method, the super absorbent polymers are distributed more evenly inside the wood pulp fibers, and the content of the super absorbent polymers are increased. Applying the current method, the highest ratio of the content of super absorbent polymers versus the content of the wood pulp fibers is 1:2. Increasing the content of super absorbent polymers in the absorbent core will result in enhanced liquid-absorbing capability of the absorbent core. A significant advantage of the present disclosure is that increase of the content of super absorbent polymers without adding wood pulp fibers, which will enable the hygiene pad to have a greater liquid-absorbing capability and to absorb liquid more consistently.

B. Compressing and embossing on the absorbent core through the following steps: the mixture of wood pulp fibers and super absorbent polymers are covered by the top tissue 8 and the bottom tissue 2, and a transitional roll 9 directs the top tissue 8 and completes a preliminary compression to form a first compressed absorbent core; a folding sector folds the edges of the first compressed absorbent core wherein the mixture of wood pulp fibers and the super absorbent polymers is completely covered by tissues, preventing any leak of wood pulp fibers or super absorbent polymers when using the hygiene pads.

Figure 5:
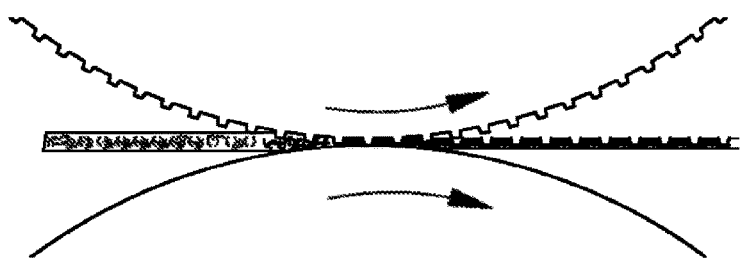
FIG. 5 is an enlarged representation showing the cross section of a top embossing roll and a bottom embossing roll through which the absorbent core is embossed and compressed.

A bottom compressing roll 11.2 and a top compressing roll 11.1 work in coordination to complete a second compression, wherein the top compressing roll 11.1 and the bottom compressing roll 11.2 may be connected to a synchronous gear ensuring that the two compressing rolls are synchronized. A bottom embossing roll 12.2 and a top embossing roll 12.1 work in coordination to complete embossing on the absorbent core. The surface of the bottom embossing roll 12.2 may be smooth and made of stainless steel and the surface of the top embossing roll 12.1 may have evenly distributed studs having a circular truncated shape. The embossing rolls may be connected to a synchronous gear to ensure that the rolls rotates at the same speed. The edge folded first compressed absorbent core goes through the gap between the compressing rolls 11.1 and 11.2 and then through the gap between the embossing rolls 12.1 and 12.2 to complete the compressing and embossing. The wood pulp fibers inside the absorbent core are instantly compressed and fixed due to the pressure and heat from the rolls. As the temperature raises, the density of the wood pulp fibers inside the absorbent core increases due to the high temperature and pressure at particular locations, and therefore the wood pulp fibers become more dense inside the absorbent core (as shown in FIG. 5). The pressure inserted on the absorbent core comes from the weight of the roll itself and the force generated by a cylinder placed on the roll, wherein the combined pressure may be 40 Mp-100 Mp, the temperature may be controlled at 120° C.-160° C., and the gap between the rolls may be 0.5-5 mm.

Figure 6:
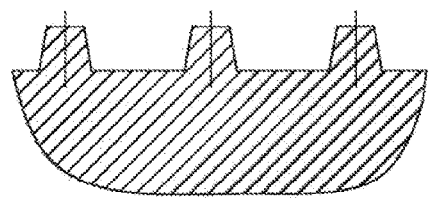
FIG. 6 is an enlarged representation showing the cross section of the surface of the top embossing roll.
Figure 7:
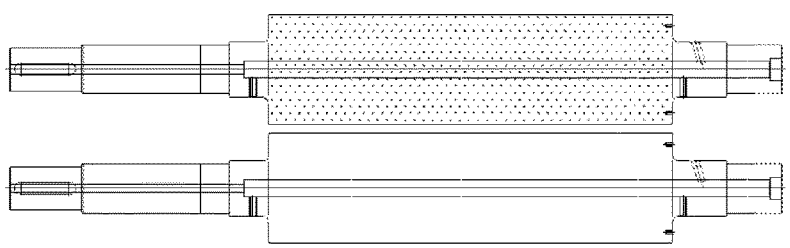
FIG. 7 is a schematic representation showing the overall coordination of the top embossing roll and the bottom embossing roll.
Figure 8:
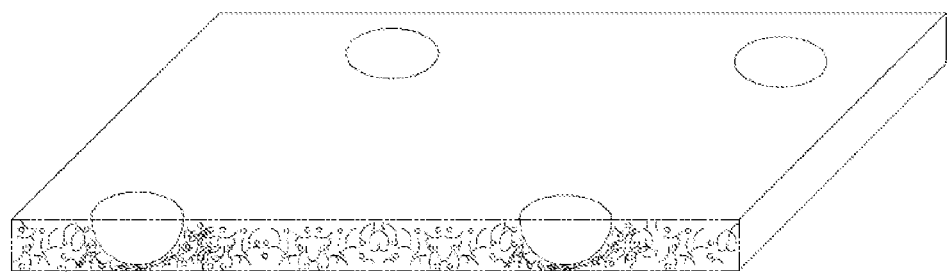
FIG. 8 is a perspective representation of the structure of the absorbent core after being embossed and compressed.
Figure 9:
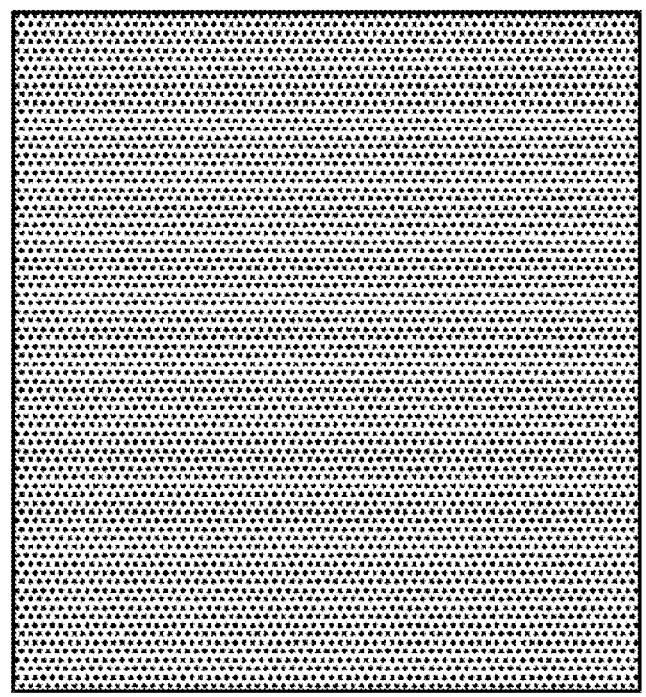
FIG. 9 is a schematic representation of a finished absorbent core product.

The absorbent core may be embossed with a honey comb structure wherein every square centimeter has 1-2 grids. This step forms a three-dimensional net structured space of the wood pulp fibers, wherein super absorbent polymers are locked in the space inside the three-dimensional net structured space so that the super absorbent polymers are prevented from sliding inside the absorbent core. This step resolves the issue that the hygiene pad is unable to absorb liquid in a consistent way. As shown in FIG. 6, the surface of the top embossing roll 12.1 has evenly distributed circular truncated shaped studs. The top diameter of the studs may be 2 mm, the bottom diameter may be 2.5 mm, and the height may be 2.2 mm. The studs may be made by chemical corrosion on a stainless steel of relatively high hardness, and the top embossing roll 12.1 may have relatively high hardness. As shown in FIG. 7, the diameter of the top embossing roll 12.1 and the diameter of the bottom embossing roll 12.2 may be the same. The width of the gap between the embossing rolls depends on the weight and thickness of the wood pulp fibers, wherein normally the width of the gap may be 0.5-5 mm, which could ensure that the absorbent core would not be twisted or deformed when it goes through the gap. The compressing roll and the embossing roll may be installed with a heating device inside each roll. As shown in FIG. 8, the density of the wood pulp fibers instantly change as the absorbent core goes through the rolls inserting pressure and high temperature, wherein such change of density significantly increased the tear strength of the absorbent core. The two embossing rolls may create a honey comb structure on the absorbent core with every square centimeter has 1-2 grids, preventing the super absorbent polymers from sliding inside the hygiene pad. This resolves the issue that the hygiene pad is unable to consistently absorb liquid. The absorbent core made by the current invention may weigh 80 grams-500 grams per square meters. The tear strength may be significantly increased due to its specially designed embossed structure as shown in FIG. 9. According to tests, the tear strength of the absorbent core along the machine direction can normally reach 0.015 KN/m.

C. Shaping of the absorbent core through the following steps: a cutter is used to cut the absorbent core into separate pieces, and the flat moving belt transports the cut absorbent core to the next step to make final hygiene products. Under the current step, a bottom cutting roll 14.2, may be made of a material of relatively high hardness and its surface may be smooth. The bottom cutting roll 14.2 works in coordination with a top cutting roll 14.1 to cut the absorbent core into separate pieces. To prevent the cutter from always cutting on the same place on the bottom cutting roll 14.2, the diameter of the top cutting roll 14.1 may be longer than the diameter of the bottom cutting roll 14.2. A first flat moving belt 13 is the platform for transporting the absorbent cores and its surface has negative pressure. The cut absorbent core 100 is transported to the next step for making finish hygiene pad products by a second flat moving belt 15.

The current invention is not limited to the preferred embodiment described above. Anything that is the same as or substantially the same as the current invention falls under the scope of the current invention, regardless of any change to certain shape or structure.

The invention claimed is:
1. A method for making absorbent cores for hygiene pads comprising the following steps:
   (a) suctioning of wood pulp fibers which are mixed with super absorbent polymers by the following process:
   moving a base tissue along on a transmitting belt on a suction bed that has negative pressure on its surface;
   shredding rolls of wood pulp into wood pulp fibers by a wood pulp shredder, the wood pulp fibers falling with the airflow inside a wood pulp fiber container;
   suctioning the wood pulp fibers on top of the base tissue by the negative pressure from the surface of the suction bed, wherein the wood pulp fibers form a net structure on top of the base tissue;
   dispensing super absorbent polymers, from a super absorbent polymer container, on top of the net structure of wood pulp fibers carried on the moving base tissue by rotation of a distributing roll,
   wherein, under the influence of negative pressure on a surface of the suction bed, the super absorbent polymers are sucked into spaces within the net structure formed by the wood pulp fibers which results in a mixture of the wood pulp fibers and the super absorbent polymers to form a super absorbent core; and
   placing a top tissue to cover the base tissue;
   (b) compressing and embossing the absorbent core by the following process:
   placing the top tissue is placed on top of the base tissue covering the mixture of the wood pulp fibers and the super absorbent polymers, wherein a transitional roll directs and positions the top tissue and completes a preliminary compression to form a first compressed absorbent core;
   transporting the first compressed absorbent core through a folding sector wherein edges of the first compressed absorbent core are folded so that the mixture of the wood pulp fibers and the super absorbent polymers are completely covered by tissues to prevent leaking of the mixture of wood pulp fibers and the super absorbent polymers when using the hygiene pads;
   compressing the edge-folded first absorbent core is compressed again by coordination of a top compressing roll and a bottom compressing roll, and then embossed by coordination of a top embossing roll and a bottom embossing roll, wherein a surface of the top embossing roll has evenly distributed studs;

creating a three dimensional net-structured space of the wood pulp fibers by embossing, wherein the super absorbent polymers are locked inside the three dimensional net-structured space;

using pressure and heat to complete compression of the absorbent core, wherein the roll's weight is used to generate pressure and forces from a cylinder attached on the roll, and the pressure created by the roll is between 40-100 Mpa;

the temperature of the heat is controlled at 120.degree. C.-160.degree. C., and the top and the bottom rolls having a separation of approximately 0.5-5 mm; and the absorbent core has embossed pattern wherein every square centimeter has 1-2 embossed grids; and (c) shaping of the absorbent core by the following process:

cutting the absorbent core into separate pieces by a cutter and using a second flat moving belt to transport the pieces, wherein the absorbent core is cut by coordination of a top cutting roll and a bottom cutting roll and the top cutting roll has a diameter that is greater than diameter a diameter of the bottom cutting roll to prevent the top cutting roll from cutting at the same place on the bottom cutting roll;

providing a first flat moving belt for transporting absorbent cores, wherein the cut absorbent core having a desired shape is transported by the second flat moving belt to the next step for making finished hygiene pads, wherein a top surface of the flat moving belt has negative pressure.

* * * * *